United States Patent [19]

O'Rourke et al.

[11] Patent Number: 6,078,728
[45] Date of Patent: Jun. 20, 2000

[54] VOLATILE CARRIER FOR USE WITH A HEATING DEVICE

[75] Inventors: Lynn M. O'Rourke, Janesville; John W. Mikkonen, Town of Mount Pleasant, County of Racine; Brian T. Davis, Burlington; John J. Gatzemeyer, Town of Caledonia, County of Racine, all of Wis.

[73] Assignee: S. C. Johnson & Son, Inc., Racine, Wis.

[21] Appl. No.: 09/102,135

[22] Filed: Jun. 22, 1998

[51] Int. Cl.⁷ .................................. F24F 6/00; F24F 6/08
[52] U.S. Cl. ............................................. 392/390; 392/395
[58] Field of Search ..................... 392/386, 387, 392/390, 391, 392, 394, 395; 261/142, 94, 99, DIG. 65; 239/44, 45, 53, 54, 55, 56, 57, 135, 136

[56] References Cited

U.S. PATENT DOCUMENTS

| | | |
|---|---|---|
| 2,103,609 | 12/1937 | Gradburn . |
| 2,624,925 | 1/1953 | Schmitz . |
| 2,931,880 | 4/1960 | Yaffe ...................................... 392/390 |
| 3,120,345 | 2/1964 | Bolger . |
| 3,441,353 | 4/1969 | Claff . |
| 3,778,924 | 12/1973 | Okui . |
| 4,556,539 | 12/1985 | Spector . |
| 4,588,874 | 5/1986 | Napierski . |
| 4,725,712 | 2/1988 | Schroeder . |
| 4,735,358 | 4/1988 | Morita et al. . |
| 4,849,181 | 7/1989 | Kelley et al. . |
| 4,849,606 | 7/1989 | Martens et al. . |
| 5,095,647 | 3/1992 | Zobele et al. . |
| 5,115,975 | 5/1992 | Shilling . |
| 5,167,877 | 12/1992 | Pai ............................................ 261/30 |
| 5,220,636 | 6/1993 | Chang ...................................... 392/390 |
| 5,222,186 | 6/1993 | Schimanski et al. . |
| 5,479,948 | 1/1996 | Counts et al. . |
| 5,695,692 | 12/1997 | Kennedy .................................... 261/30 |
| 5,805,768 | 9/1998 | Schwartz et al. ....................... 392/390 |

FOREIGN PATENT DOCUMENTS

| | | |
|---|---|---|
| 671123 | 9/1995 | European Pat. Off. . |
| 2547735 | 6/1984 | France . |
| 2547734 | 12/1984 | France . |
| 45-19801 | 8/1970 | Japan . |
| 53-98275 | 8/1978 | Japan . |
| 59-159728 | 9/1984 | Japan . |
| 62-36001 | 3/1987 | Japan . |
| 62-187583 | 11/1987 | Japan . |
| 62-190483 | 12/1987 | Japan . |
| 63-192445 | 8/1988 | Japan . |
| 1-117346 | 8/1989 | Japan . |
| 1-210488 | 8/1989 | Japan . |
| 3-97464 | 4/1991 | Japan . |
| 3-118749 | 12/1991 | Japan . |
| 2122903A | 1/1984 | United Kingdom . |
| 96/03880 | 2/1996 | WIPO . |
| 96/28970 | 9/1996 | WIPO . |

*Primary Examiner*—Sang Paik

[57] ABSTRACT

A volatile carrier for supplying a volatile ingredient to a heating device to be dispensed thereby, the heating device having a heat transfer site and a pass-through path to receive an inserted volatile carrier at one end of the pass-through path to position the volatile carrier adjacent to the heat transfer site. The volatile carrier has a substantially unitary reservoir block containing a supply of the volatile ingredient. The reservoir block is greater in size than the heat transfer site. An advancement device is supplied by which a user can manually advance the reservoir block past the heat transfer site to expose different portions of the reservoir block to heat. A method of supplying a volatile ingredient to such a heating device by use of such a volatile carrier is also described.

26 Claims, 3 Drawing Sheets

VOLATILE CARRIER FOR USE WITH A HEATING DEVICE

BACKGROUND OF THE INVENTION

This invention relates to vapor releasing devices. More particularly, it relates to devices and methods for supplying vaporizable materials to a heater to allow the materials to be dispensed into the air.

It is well known to provide vapor releasing materials from mats and other carriers that are positionable in a heating device so as to cause the materials to vaporize. See e.g. Martens, III. et al., U.S. Pat. No. 4,849,606 (The disclosures of U.S. Pat. No. 4,849,606 and all other patents and patent applications referred to herein are incorporated by reference). These devices are effective for dispensing various volatile materials, including such materials as insect control active ingredients and scents for room freshening. Typically, the carriers must replaced from time to time to renew the source of volatile material. In many applications, it is desirable to extend the useful life of carriers so as to extend the time before replacement is necessary.

In addition, there are many insect control heating devices that have been and are being marketed that are designed to accept conventional mats loaded with mosquito or other insect control materials. Many of these devices have a containing well, trough, or chamber that the mat slides into to be held over a hot surface or other source of heat. The exact size and shape of these containing structures differ somewhat from device to device. Thus, it would be desirable not only to have a volatile ingredient carrier having an extended useful life but also one that can fit securely into chambers of differing sizes.

Addressing the need for extended life, Petrillo, French Pat. No. 2,547,735 discloses a dispensing system that utilizes a series of connected tablets. The tablets are sequentially moved over a heater, with the next tablet moved over the heater when the previous tablet has been used up. Unfortunately, this dispensing system has an indexing system that is costly to manufacture and that is restricted to use with specifically designed heater openings. Other systems rely on reel-to-reel tape systems that also can be costly and are limited to specifically designed heating devices. There are many examples of such tape systems, but see, as one example, Japanese Pat. Appl. No. JP 1-210488, which also allows a user to select between different volatile materials. Zobele and Pedrotti, WO 96/28970 provides a polymer block that is treated with insecticide and held within a frame. The block can carry sufficient insecticide to last for a considerable period of time.

To obtain a long-lasting source of vaporizable active ingredient, other products provide for a wick that delivers a liquid vaporizable material from a reservoir to a heater. See, for example, Zobele et al., U.S. Pat. No. 5,095,647, and Schimanski et al., U.S. Pat. No. 5,222,186. A commercially available heater device manufactured by Zobele Industrie Chimiche S.P.A., Italy, as Zobele heater model SCJ-009 has a vertical passage extending through a heated ceramic block. S. C. Johnson & Son, Inc. of Racine, Wisconsin, sells a volatile supplier for this heater device that has a bottle containing a liquid insect control preparation, the bottle having an upwardly extending wick that fits through the heater's vertical passage when the bottle is attached to the underside of the heater device. This arrangement is effective but does require the use of liquid, which is subject to spilling and the like. In contrast, the volatilizing device shown in Martens, III. et al., U.S. Pat. No. 4,849,606 heats a volatilizable gel contained within a plastic tray that is closed with a volatiletransmitting membrane.

A need exists for improved devices and methods for supplying providing vaporizable materials to heaters.

BRIEF SUMMARY OF THE INVENTION

In one aspect, the invention provides a volatile carrier for supplying a volatile ingredient to a heating device to be dispensed thereby. The heating devices with which use of the volatile carrier is intended are of the kind that have a heat transfer site and a pass-through path to receive a volatile carrier inserted at one end of the pass-through path to position the volatile carrier adjacent to the heat transfer site. Heat in these devices may be generated electrically, by flaming or catalytically combusted fuel, or by any other of the ways known to those skilled in the art to provide heat in such devices. Such heating devices commonly are used for dispensing air quality modifying materials such as perfumes, insect control ingredients, and any other volatile material to be dispensed, if the material is capable of withstanding the temperatures of such a device. "Volatile ingredient" is defined to include all such materials. "Insect control ingredient" includes materials that kill insects as well as those that otherwise affect their biological functions or behavior, including bpt not limited to insecticides, insect repellents, and insect growth inhibitors.

The volatile carrier of the invention includes a substantially unitary reservoir block containing a supply of the volatile ingredient to be dispensed. The term "block" is not intended to connote any particular shape. Instead, "block" includes any substantially unitary mass of non-flowable material, including fibrous mats, non-flowing gels, plastic or other solid materials, and the like. A reservoir block is defined to be "substantially unitary" if it is a mass of material functionally uninterrupted with respect to the release of volatile ingredients, even if the block is made up of sections that, while they are closely grouped and preferably at least abut each other, are not joined into an unbroken monolith of material. But preferably, the reservoir block is a single, undivided block of material and most preferably is made of a polymer capable of receiving the volatile ingredient and releasing it when subjected to the heat of the heating device. However, other convenient materials formable into blocks and suitable as substrates for the heated release of volatile ingredients may be used instead. Preferably, the reservoir block does not deform as a consequence of its being handled during use. The reservoir block also may be made of materials that consume as the volatile ingredient is released.

The reservoir block of the invention is greater in size than the heat transfer site of the heating device with which it is to be used. The invention includes an advancement device by which a user can manually advance the reservoir block past the heat transfer site to expose different portions of the reservoir block to heat.

Different selected regions of the reservoir block can carry different volatile ingredients, different concentrations of the same volatile ingredient, or combinations of such variations. This allows a user to use a single volatile carrier and, by using the advancement device, to position a selected portion of the reservoir block by the heat transfer site to select among differing volatile ingredients or delivery amounts or rates. For example, a high concentration insect control ingredient can be useful at night, when mosquito activity is high, and a lower concentration, a different insect control ingredient, or only a scent may be appropriate during the day.

Preferably, the advancement device of the volatile carrier provides a signal to a user that correlates with movement of the reservoir block as the reservoir block is moved past the heat transfer site. The signal can be a click or other noise, a tactile signal such as that a user can feel when the resistance of a detent is overcome by manually manipulating a moving part, or a visual signal such as the appearance of different colored materials as they are moved behind a window or the appearance of a line or other visual indicia or indicator that is moved or distinctively aligned. Other signals will be apparent to those skilled in the art and fall within the breadth and scope of the invention. Preferably, movement of the reservoir block is by discrete increments, most preferably with each incremental movement accompanied by such a signal.

In one aspect of the invention, the advancement device includes a frame that holds the reservoir block. Preferably, the frame has a handle by which a user can manipulate the volatile carrier and is sufficiently flexible to follow slight bends in a pass-through path.

Many heating devices for dispensing volatile ingredients are so designed as to allow a volatile carrier to be inserted in one end of a pass-through path and to exit the heating device at the other end of the pass-through path. Also, independent of the exiting feature just mentioned, heating devices exist that employ enclosed passages, tunnels, or chambers; open troughs; or other arrangements as the pass-through path, the lateral dimensions of such pass-through paths typically being defined by path sides. In another aspect of the invention, the volatile carrier of the invention especially suited to such heating devices includes a longitudinally extended frame having a plurality of resilient fingers that extend distally from the frame to engage a path side to position the frame with respect to the path side and the heat transfer site. Preferably, resilient fingers extend from the frame to engage opposed path sides.

Preferably, the fingers slant at an angle away from the intended direction of travel of the volatile carrier through the pass-through path to favor movement of the volatile carrier in only the intended direction. In a further aspect of the invention, the frame includes a stop tab that extends distally from the frame sufficiently far to restrict and preferably even prevent the volatile carrier from entering the pass-through path of the heater device beyond the location of the stop tab. This arrangement, when combined with the slanted fingers just described, favors movement of the volatile carrier one way through the pass-through path until the volatile carrier is stopped and held by the stop tab, whereupon accidental or unintentional release of the volatile carrier from the heater device is discouraged. However, the stop tab preferably is manually bendable in a proximal direction sufficiently far to allow a user to intentionally move the volatile carrier on through the pass-through path. The stop tabs may be either resilient or not, as desired, and may be lockable in place when bent to a proximal location. Resilient but lockable stop tabs are preferred.

In another aspect of the invention, the volatile carrier described is particularly suited for use with a heater device whose pass-through path has a pinch point of a given width and thereafter either opens to a wider dimension or ends in an open exit. It is preferred that the fingers of the volatile carrier extend sufficiently distally that the fingers engage a path side at the pinch point to require the fingers to bend proximally, bending away from the direction of movement of the volatile carrier through the pass-through path. The fingers then resiliently spring distally after passing the pinch point.

If, as is preferred, the fingers are longitudinally spaced along the frame and are sufficiently resilient and stiff that a user can hear audible clicks as successive fingers resiliently spring back distally after passing the pinch point, this effect provides a signal to the user that corresponds to incremental movement of the reservoir block past the heat transfer site.

As has been previously mentioned, some existing heating devices have a pass-through path that is a passage extending upwardly through a heated block of ceramic or other material. An embodiment of the invention especially useful with such heating devices, but also with other arrangements where a heating device is so designed as to allow the reservoir block to exit the heating device at the other end of the pass-through path, includes a longitudinally extended reservoir block, preferably made of a material that can resist deformation, at least to the extent necessary to avoid the reservoir block's deforming and jamming as it passes through the pass-through path. A block container is secured to a first end of the reservoir block, the block container being attachable to the heater device, with a second end of the reservoir block aligned with and insertable into the pass-through path. The reservoir block is designed to be movable with respect to the block container to advance the reservoir block past the heat transfer site.

Preferably the block container includes a shell that attaches to the heater device and a manually operable block advancer that a user can operate to advance the reservoir block into the pass-through path. To achieve this, the block advancer can include a block holder that operates on the first end of the reservoir block and is slidably engaged with the shell so that, when a user slides the block holder relative to the shell, the reservoir block moves past the heat transfer site. In another and preferred arrangement, the block advancer is operated by a user by rotating a knob or other rotatable part that is rotatably engaged with the shell such that, when a user turns the rotatable part, the reservoir block is moved relative to the heat transfer site.

In any event, preferably the block advancer provides a signal to a user that corresponds to movement of the reservoir block as the reservoir block is advanced past the heat transfer site. For example, when the block advancer has a knob or other rotatable part that is turned to move the reservoir block, it is preferred to provide a detent mechanism that overcomeably resists movement of the rotatable part as it is turned in successive, incremental amounts to provide a click or a tactile signal of an incremental movement of the reservoir block.

When a rotatable part arrangement is used, the block advancer preferably includes a threaded shaft rotatably engaged but longitudinally fixed with respect to the shell, and a nut longitudinally fixed with respect to the reservoir block and threadably engaged with the threaded shaft. When the threaded shaft is rotated with respect to the nut, the reservoir block is moved longitudinally relative to the shell to move past the heat transfer site. Alternatively, the reverse arrangement can be used, wherein the block advancer includes a nut rotatably engaged but longitudinally fixed with respect to the shell, and a threaded shaft longitudinally fixed with respect to the reservoir block and threadably engaged with the nut. When the nut is rotated with respect to the threaded shaft, the reservoir block will move longitudinally relative to the shell.

The method of the invention of supplying a volatile ingredient to be dispensed by heating devices of the sort referred to above includes the steps of supplying a volatile carrier as described above and moving the reservoir block past the heating device's heat transfer site. When a reservoir block is provided having regions carrying different volatile ingredients, the step of moving the reservoir block past the heating device's heat transfer site can include the steps of selecting a region of the reservoir block carrying a desired volatile ingredient and moving that region to the heat transfer site. The method may further include the step of successively moving different selected regions of the reservoir block to the heat transfer site to cause the heating device successively to emit different volatile ingredients.

When a reservoir block is provided having regions carrying different concentrations of the same volatile ingredient, the step of moving the reservoir block past the heating device's heat transfer site can include the steps of selecting a region of the reservoir block carrying a desired concentration of the volatile ingredient and moving that region to the heat transfer site to cause the heating device to emit a selected amount of the volatile ingredient. The method may further include the step of successively moving different selected regions of the reservoir block to the heat transfer site to cause the heating device successively to emit differing amounts of the volatile ingredient.

DESCRIPTION OF THE PREFERRED EMBODIMENTS

Figures 1, 2:
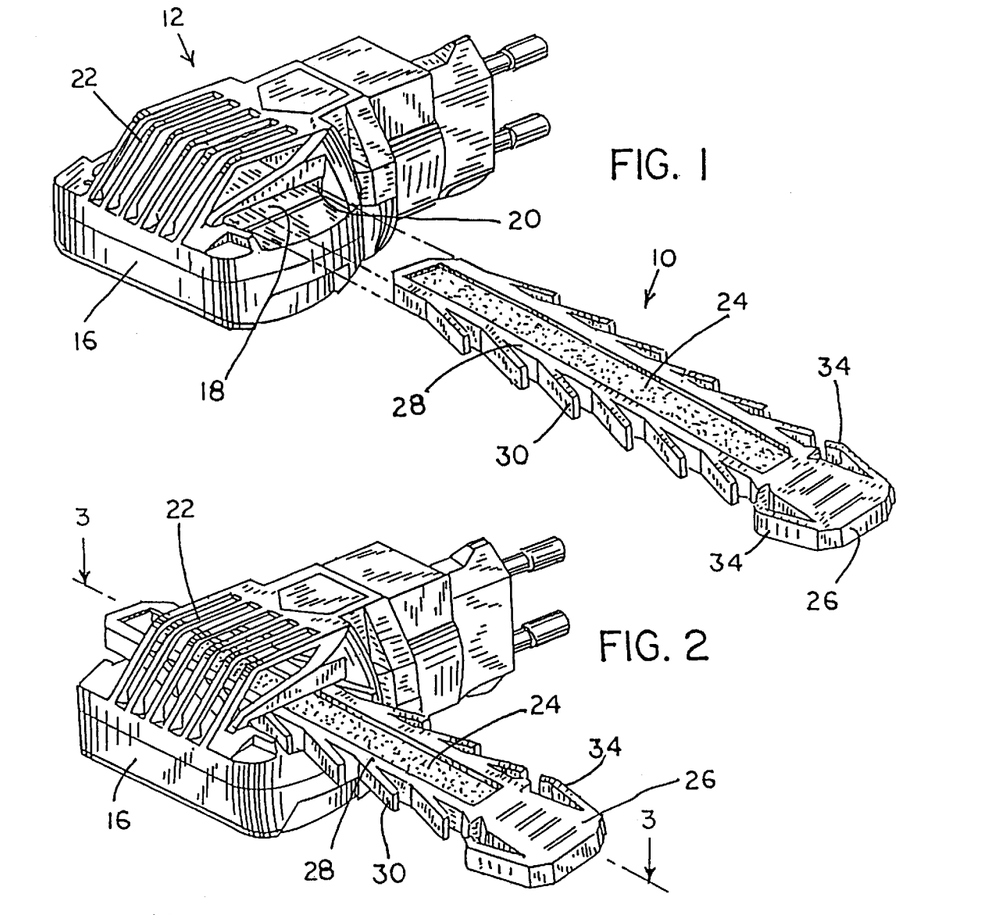
FIG. 1 is a front perspective view, from above and to one side, of a volatile carrier of the invention, shown positioned beside a conventional heating device.
FIG. 2 is the volatile carrier of FIG. 1, shown inserted into the heating device shown in FIG. 1.

Turning now to the drawings, wherein like reference numbers refer to like and corresponding parts throughout the several views, a first embodiment of the volatile carrier of the invention is shown generally at 10 in FIG. 1. The volatile carrier 10 is shown positioned beside a conventional heating device, shown generally at 12.

Heating devices for vaporizing volatile ingredients are well known as are, specifically, heating devices that volatilize insect control ingredients from fiber mats or liquid-bearing wicks. The conventional heating device 12 corresponds generally to the commercially available heater model SCJ-009 made by Zobele Industrie Chimiche S.P.A., Italy, and sold by S. C. Johnson & Son, Inc., of Racine, Wisconsin. The SCJ-009 device is preferred for use with the specific embodiments of the invention described below, but the invention is in no way limited to use with the SCJ-009 device. To the contrary, the volatile carrier 10 is designed to be flexibly usable with a variety of mat or wick-type heating devices, serving as an alternative to conventional mat or liquid-bearing wick arrangements.

The heating device 12 is designed to be plugged into an electrical receptacle. Heat is generated by a resistance or other electrical heater (not shown) that is located within a ceramic block (best seen at 13 in FIG. 6 in conjunction with a second embodiment of the volatile carrier, yet to be discussed). The ceramic block 13 becomes hot when the heating device is energized. The top surface 14 (seen in FIG. 3) of the ceramic block 13 is exposed and is adapted to receive a mat or other carrier of volatile ingredients to be dispensed. The top surface 14 serves as a heat transfer site, the site at which heat is transferred to a mat or other volatile-holding carrier. In general, all conventional heating devices of this sort make provision for the transfer of heat from some heat source to the mat or other volatile-holding carrier used with the heating device. The location of that heat transfer typically is limited in size by use of a heated plate or passageway, a grid of a selected dimension placed over a catalytic heater, or the like. The term "heat transfer site" as used herein refers to the location of heat transfer and is referred to as having an essentially fixed area.

The heating device 12 is also typical of many conventional heating devices in that it has a body 16 having a pass-through path 18 having path sides 20. Commonly, a mat or other conventional volatile-holding carrier is inserted in or on the heating device, to slide into the device until the carrier reaches the heat transfer site. A common arrangement is to replace a spent mat, for example, by moving it on out of the heating device, pushing it with a new, fresh mat. The pass-through path defines the route followed through the heating device 12 by such a mat or other volatile-holding carrier, and the path sides 20 serve as guides, ensuring that the carrier is properly located at the heat transfer site.

The pass-through path 18 of the heating device 12 allows insertion of a mat from the side of the heating device under a protective grid 22, with spent mats being pushed out of the opposite side of the heating device when a fresh mat is inserted in the pass-through path. The heating device 12 may also be equipped with alternative pass-through paths, such as the vertical passage shown at 42 in FIG. 6 and discussed below.

The volatile carrier 10 has a substantially unitary reservoir block 24 (as "substantially unitary" and "block" are defined, above) containing a supply of a volatile ingredient. The reservoir block 24 is longitudinally extended and is greater in size than the heating device's that transfer site. The reservoir block 24 preferably is composed of a polyether-polyamide copolymer obtained through the linear regular polymerization of polyether segments alternated with polyamide segments. Such compounds have excellent chemical and mechanical properties for this application and are available on the market under various commercial names. This material is preferred in part because its mechanical characteristics allow it to be formed into a variety of useful shapes by casting, extrusion, injection molding, sheet casting, or other conventional forming methods.

Polyether-polyamide copolymer materials can be impregnated with insect control or other volatile ingredients by placing them in an appropriate solution of the volatile ingredients. See Pedrotti, EP 671,123 regarding techniques for forming such volatile releasing substrates for use with heaters. By selecting various relative percentages of the polyether and polyamide fractions of the copolymer, one can select for different volatile ingredient loading and retention characteristics.

Insect control ingredients are the preferred volatile ingredients. Different regions of the reservoir block 24 can be treated with differing concentrations of ingredient or with different ingredients. Useful insect control ingredients include but are not limited to organo phosphorous insecticides, lipidamide insecticides, natural repellents such as citronella oil, natural pyrethrums and pyrethrum extract, and synthetic pyrethroids. The synthetic pyrethroid esbiothrin is particularly preferred, used with a polymeric reservoir block made of the polyether-polyamide copolymers known commercially as Pebax 4033 and Pebax 3533 (available from Zobele Industrie Chimiche S.P.A.).

The volatile carrier 10 includes a handle 26 that serves as an advancement device by which a user can manually advance the reservoir block 24 past the heat transfer site of the heating device 12. By using the handle 26, a user can move selected parts of the reservoir block 24 to the heat transfer site to expose different portions of the reservoir block to heat.

The volatile carrier 10 has a frame 28 that holds the reservoir block, the handle 26 preferably being a part of the frame. Preferably, as in the embodiment shown at 10, the frame 28 is longitudinally extended and has a plurality of resilient fingers 30. The resilient fingers 30 extend distally from the frame, preferably extending sidewardly from at least one and preferably from two opposite sides of the frame.

Whether located on only one side or on opposite sides of the frame 28, the resilient fingers 30 are sufficiently long to engage at least one and preferably opposing path sides 20 of the pass-through path 18 of a heating device 12. The resilient fingers 30 thus position the frame 28 within the pass-through path 18. Because the fingers 30 are resilient, they can operate within pass-through paths of different heating devices, flexing to fit various path widths and to move past indentations and projections that may exist within such pass-through paths.

Preferably, as in the volatile carrier shown at 10, the resilient fingers 30 slant at an angle away from the intended direction of travel of the volatile carrier through a pass-through path. This arrangement favors movement of the volatile carrier in only the intended direction.

Figure 3:
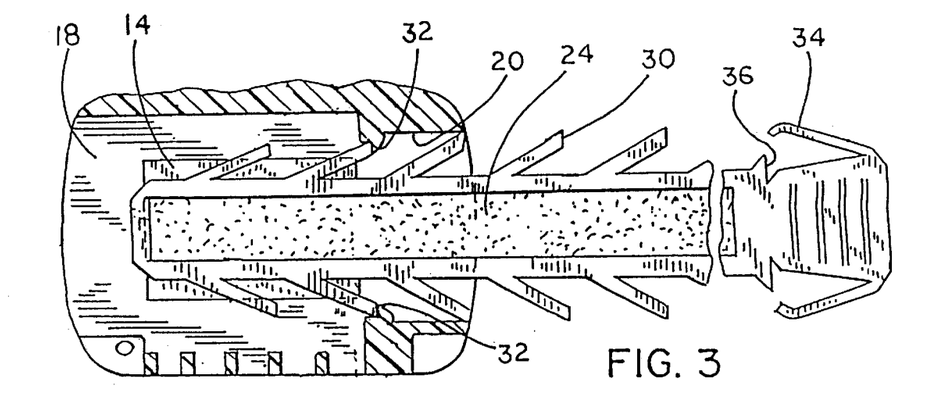
FIG. 3 is a cross sectional view of the volatile carrier of FIG. 2, partially inserted into the heating device shown in FIG. 2 (with only a broken away portion of the heating device shown), the view taken along section line 3—3 of FIG. 2.

The pass-through path 18 of heater device 12 has a pinch point 32 of a given, constrained width and thereafter opens to a wider dimension. In other conventional heater devices, the pass-through path may be all of one width, making the entire length of the path the "pinch point" that opens to a wider dimension simply by ending with an exit. The resilient fingers 30 extend sufficiently distally that the fingers engage a path side 20 at the pinch point 32, requiring the fingers to bend proximally, toward the frame 28, in a direction slanting away from the direction of movement of the volatile carrier 10 through the pass-through path. Once past the pinch point 32, the fingers 30 resiliently spring back distally.

The fingers 30 of the preferred embodiment shown are longitudinally spaced along the frame 28 and are sufficiently resilient and stiff that a user can hear audible clicks or feel tactile impulses as successive fingers spring distally as they pass the pinch point. As a result, the user receives a signal that corresponds to incremental movement of the reservoir block 24 past the heat transfer site.

Preferably, as in the embodiment shown, at least one and preferably two stop tabs 34 extend distally from the frame 28, preferably generally at the location of the handle 26 and preferably slanting in the intended direction of travel of the volatile carrier 10. The stop tabs 34 extend distally from the frame 28 sufficiently far to prevent the volatile carrier 10 from entering the pass-through path 18 beyond the location of the stop tabs. A user can pinch the stop tabs 34 inwardly, bending them proximally sufficiently to allow a user to intentionally move the volatile carrier 10 on through the pass-through path 18. Preferably the stop tabs 34 either non-resiliently bend or lock in the bent position with a width narrower than the narrowest pinch point of the pass-through path 18 to allow the volatile carrier 10 to freely pass from the heating device 12. In the preferred embodiment shown, the distal ends of the stop tabs 34 contact an engaging surface 36 and lock in their bent position.

Figure 4:
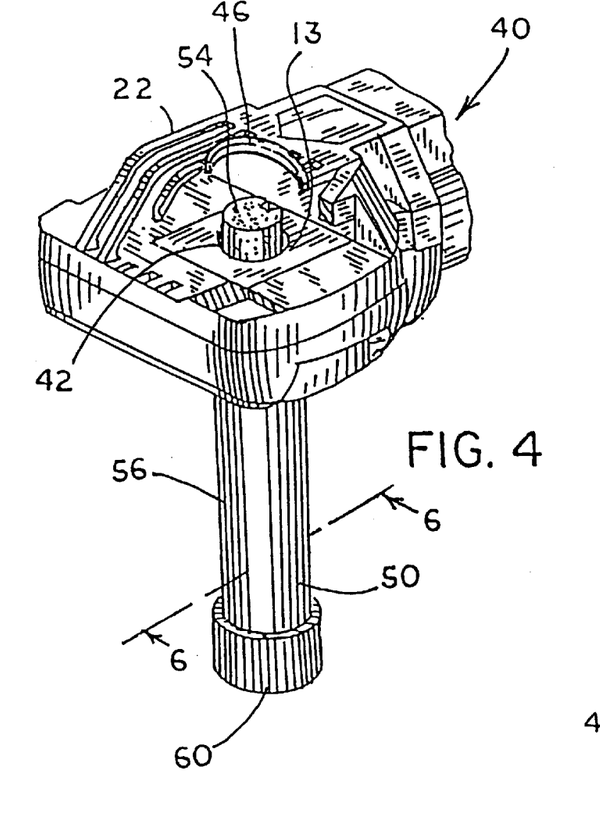
FIG. 4 is a perspective view, from above and to one side, of an alternative embodiment of the volatile carrier of the invention, shown positioned in a conventional heating device.
Figure 5:
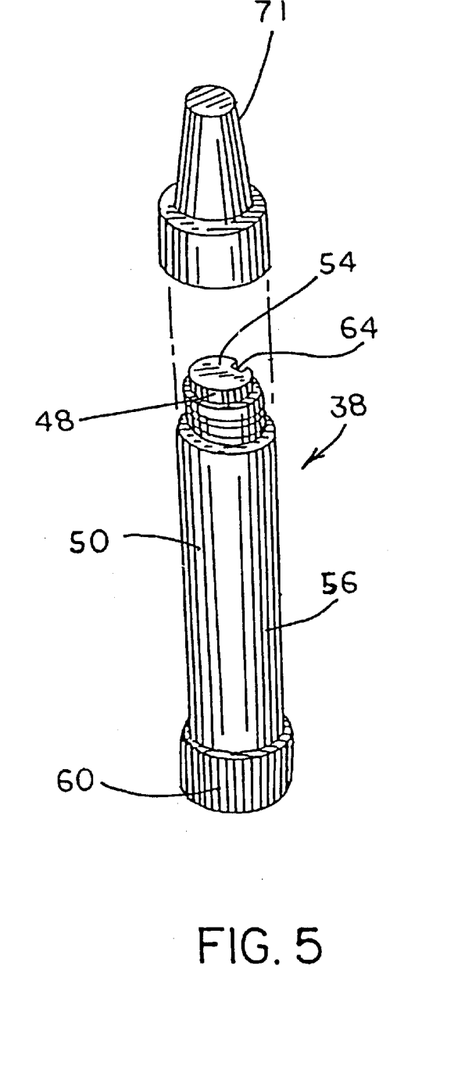
FIG. 5 is a perspective view, from above and to one side, of the volatile carrier of FIG. 4, shown with a protective cap.

A second embodiment of the volatile carrier of the invention is shown generally at 38 in FIG. 5. The second embodiment 38 is shown in FIG. 4 in use with heating device 40, which is generally comparable to the heating device 12, described above. Corresponding parts of heating devices 12 and 40 will be given the identical reference numbers and will not be discussed separately. Heating device 40 differs from heating device 12 in that the ceramic block 13 has a generally vertical passage 42 extending therethrough, the body 16 having an entrance port 44 (visible in FIG. 6) directly beneath the passage and the grid 22 having a corresponding exit port 46 (shown in FIG. 4) directly above the passage. The passage 42 can be used as a pass-through path, with the walls of the passage within the ceramic block 13 being the heat transfer site. The passage 42 as described is a pass-through path that can receive a reservoir block inserted at one end, with the heating device 40 being so designed as to allow the reservoir block to exit the heating device at the other end of the pass-through path.

The second embodiment 38 of the volatile carrier of the invention has a columnar reservoir block 48 that is longitudinally extended. The second embodiment 38 includes a block container 50 secured to a first end 52 of the reservoir block 48, the block container capable of substantially containing the reservoir block. The block container 50 is attachable to the heater device 40, with a second end 54 of the columnar reservoir block 48 aligned with and insertable into the passage 42. The reservoir block 48 is longitudinally movable with respect to the block container 50 by a manually operable block advancer, so that the reservoir block can be manually advanced into the passage 42 and past the heat transfer site.

Figure 6:
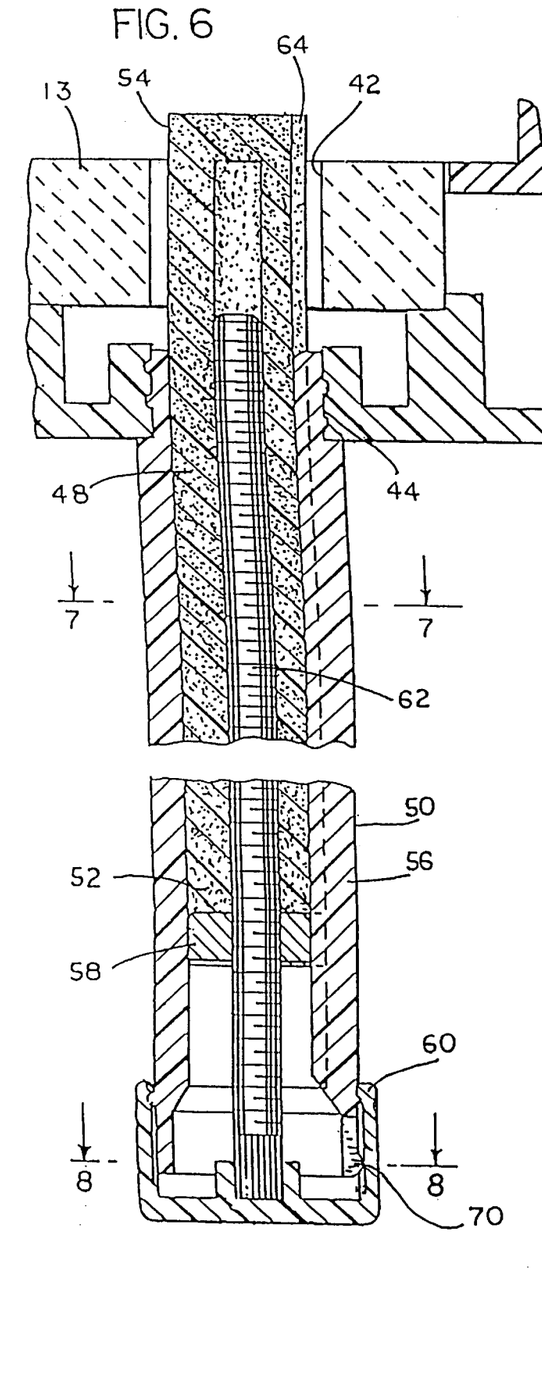
FIG. 6 is a cross sectional view of the volatile carrier and conventional heating device shown in FIG. 4, taken along section line 6—6 of FIG. 4.

Preferably the block container 50 includes a shell 56 that attaches at the entrance port 44. Preferably a block holder comparable to that shown at 58 in FIG. 6 is attached to or at least is operably related to the first end 52 of the reservoir block 48. Preferably the shell 56 and the entrance port 44 have threads and attach in threaded relation, although bayonet, snap, friction, or other attachment mechanisms well known to those skilled in the art may be used instead. The block advancer preferably forms a part of the block container 50. The block holder 58 can be designed to be slidably engaged with the shell 56 (by simply sliding within the shell or by some other conventional arrangement, not shown), with provision made (not shown) for a user to slide the block holder relative to the shell to move the reservoir block past the heat transfer site.

However, preferably the block advancer includes a knob 60 that is longitudinally fixed but rotatably engaged to the shell 56 and that, when turned relative to the shell, moves the reservoir block 48 past the heat transfer site. A threaded shaft 62 extends parallel to the longitudinal axis of the reservoir block 48 and preferably is fixedly attached to the knob 60, thereby being attached to the shell 56 in longitudinally fixed, rotating relation. The threaded shaft 62 is threadedly engaged with the reservoir block 48, either directly or by way of threaded engagement with the block holder 58. The threaded portion of the reservoir block 48 or block holder 58 constitutes a nut attached to the reservoir block in both longitudinally and rotationally fixed relation.

Figure 7:
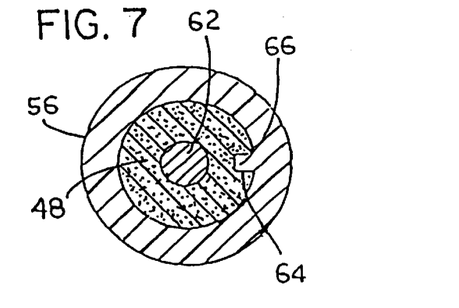
FIG. 7 is a cross sectional view of the volatile carrier shown in FIG. 6, taken along section line 7—7 of FIG. 6.

The reservoir block 48 (either directly or via the block holder 58) can be secured from rotating within the shell 56 by a longitudinally extending slot 64 in the reservoir block and/or the block holder engaging a longitudinally extending rib 66 on the shell, as is shown in FIGS. 6 and 7. That and alternative arrangements to secure a structure such as the reservoir block 48 from turning within a structure such as the shell 56 are well known to the art. Then, when the knob 60 and attached threaded shaft 62 are rotated, the reservoir block 48 will move longitudinally. Similarly, the reservoir block 48 can be moved by the knob 60 if the threaded shaft 62 is fixedly attached to the reservoir block (either directly or via the block holder 58) and is threadedly engaged in the knob. In this arrangement, the knob functions as a nut, turning in threaded relation on the threaded shaft.

Figure 8:
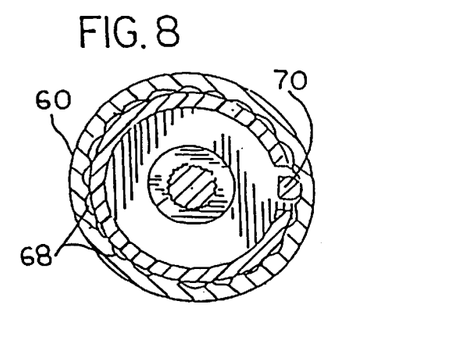
FIG. 8 is a second cross sectional view of the volatile carrier shown in FIG. 6, taken along section line 8—8 of FIG. 6.

It is desirable that the block advancer provide a signal to a user that corresponds to movement of the reservoir block as it is advanced past the heat transfer site. Preferably the block advancer includes a detent mechanism that overcomeably resists turning movement of the knob 60 relative to the shell 56 as the knob is turned in successive, incremental amounts. For example, interior surfaces of the knob 60 may have scallops 68 that present toward the shell 56, and the shell may have a spring 70 biased toward and slideably engaged in the scallops, as is best shown in FIG. 8. As the knob 60 is turned, the spring 70 snaps from scallop 68 to succeeding scallop to provide a tactile signal to a user of an incremental movement of the knob 60 and therefore of the reservoir block 48.

Figure 9:
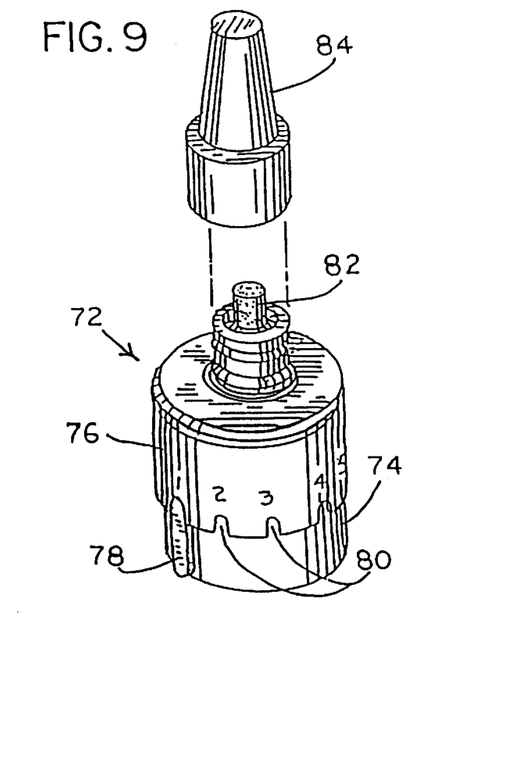
FIG. 9 is a perspective view, from above and to the front, of a third embodiment of the volatile carrier of the invention, shown with a protective cap.

A third embodiment of the volatile carrier of the invention is shown generally at 72 in FIG. 9. Parts and features of the third embodiment 72 that directly correspond to those of the first and second embodiments 10,38 will be given like reference numbers and will not be separately discussed. The third embodiment 72 is used generally in the same way as the second embodiment 38, just described, except that a knob 74 (functionally corresponding to the knob 60 of the second embodiment 38) is internally mounted within a shell 76 (that functionally corresponds to the shell 56 of the second embodiment). A lug 78 projects from the knob 74 to releasably engage notches 80 formed in the shell 76 and thus provide a tactile and visual signal of incremental advance of a reservoir block 82 (which corresponds to the reservoir block 48 of the second embodiment). The notches 80 may be marked with written indicia, such as the numbers shown in FIG. 9, to signal a user to advance the reservoir block 82, purely as a non-limiting example, perhaps once every evening to introduce a fresh portion of the reservoir block to the heat transfer site, releasing a nightly amount of an insect control ingredient. Various mechanisms for advancing the reservoir block 82 by turning the knob 74 43 will be apparent to one skilled in the art and can generally correspond to the structures disclosed with respect to the second embodiment 38.

Both the second and third embodiments 38,72 are provided with removable caps 71,84 that cover their respective reservoir blocks prior to use to avoid the premature loss of volatile active ingredient.

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

INDUSTRIAL APPLICABILITY

The volatile carrier of the invention is useful for supplying volatile ingredients to appropriate dispensers, which ingredients are useful for controlling insects, scenting or deodorizing the air, and for other purposes.

What is claimed is:

1. A volatile carrier for supplying a volatile ingredient to a heating device to be dispensed thereby, the heating device having a pass-through path in the form of a pathway selected from the group consisting of passages, tunnels, chambers, and open troughs, the pass-through path having an end opening suitable to receive an inserted volatile carrier so as to position the volatile carrier adjacent to a heat source of the heating device, the volatile carrier comprising
   a. a substantially unitary reservoir block containing a supply of the volatile ingredient; and
   b. a one-way advancement device by which a user can manually advance the reservoir block past the heat source to expose different portions of the reservoir block to heat.

2. The volatile carrier of claim 1, wherein the volatile ingredient is an insect control ingredient.

3. The volatile carrier of claim 1, wherein different regions of the reservoir block carry different volatile ingredients.

4. The volatile carrier of claim 1, wherein different regions of the reservoir block carry different concentrations of the volatile ingredient.

5. The volatile carrier of claim 1, wherein the advancement device provides a signal to a user that corresponds to movement of the reservoir block as the reservoir block is moved past the heat source.

6. The volatile carrier of claim 5, wherein movement of the reservoir block is by discrete increments.

7. The volatile carrier of claim 1, wherein the advancement device includes a frame that holds the reservoir block, the frame having a handle by which a user can manipulate the volatile carrier.

8. A volatile carrier for supplying a volatile ingredient to a heating device to be dispensed thereby, the heating device having a pass-through path in the form of a pathway selected from the group consisting of passages, tunnels, chambers, and open troughs, the pass-through path having an end opening suitable to receive an inserted volatile carrier so as to position the volatile carrier adjacent to a heat source of the heating device, the volatile carrier comprising
   a. a substantially unitary reservoir block containing a supply of the volatile ingredient; and
   b. an advancement device by which a user can manually advance the reservoir block past the heat source to expose different portions of the reservoir block to heat;
   the volatile carrier being for use with a heating device whose pass-through path has path sides, the volatile carrier including a longitudinally extended frame having a plurality of resilient fingers that extend distally from the frame to engage a path side to position the frame with respect to the path side and the heat source.

9. The volatile carrier of claim 8 for use with a heating device so designed as to allow the volatile carrier to be inserted in one end of the pass-through path and to exit the heating device at an opposite end of the pass-through path, wherein the fingers, when inserted in the pass-through path, slant at an angle away from the intended direction of travel of the volatile carrier through the pass-through path to favor movement of the volatile carrier in only the intended direction.

10. The volatile carrier of claim 9, wherein the fingers are permanently slanted at an angle away from the intended direction of travel of the volatile carrier through the pass-through path.

11. The volatile carrier of claim 9, wherein the frame includes a stop tab that extends distally from the frame sufficiently far so as to restrict the volatile carrier from entering the pass-through path beyond the location of the stop tab, the stop tab being manually bendable proximally sufficiently to allow a user to intentionally move the volatile carrier on through the pass-through path.

12. The volatile carrier of claim 8 for use with a heating device so designed as to allow the volatile carrier to be inserted in one end of the pass-through path and to exit the heating device at an opposite end of the pass-through path, the pass-through path having a pinch point of a given width and thereafter either ending or opening to a wider dimension, the fingers of the volatile carrier extending sufficiently distally that the fingers engage a path side at the pinch point to require the fingers to bend proximally and away from the direction of movement of the volatile carrier through the pass-through path, the fingers then resiliently springing distally after passing the pinch point.

13. The volatile carrier of claim 12 wherein the fingers are longitudinally spaced along the frame and are sufficiently resilient and stiff that a user can hear audible clicks as successive fingers resiliently spring back distally after passing the pinch point to provide a signal to the user that corresponds to incremental movement of the reservoir block as the reservoir block is advanced through the heat transfer site.

14. The volatile carrier of claim 8, wherein fingers extend distally from opposite sides of the frame.

15. A volatile carrier for supplying a volatile ingredient to a heating device to be dispensed thereby, the heating device having a pass-through path in the form of a pathway selected from the group consisting of passages, tunnels, chambers, and open troughs, the pass-through path having an end opening suitable to receive an inserted volatile carrier so as to position the volatile carrier adjacent to a heat source of the heating device, the volatile carrier comprising a. a substantially unitary reservoir block containing a supply of the volatile ingredient; and
  b. an advancement device by which a user can manually advance the reservoir block past the heat source to expose different portions of the reservoir block to heat; wherein the volatile carrier is suitable for use with a heating device that has a pass-through path to receive a reservoir block inserted at one end of the pass-through path, thereby positioning the volatile carrier adjacent to the heat source, the heating device being so designed as to allow the reservoir block to exit the heating device at an opposite end of the pass-through path, wherein the reservoir block is longitudinally extended and the volatile carrier includes a block container secured to a first end of the reservoir block, the block container being attachable to the heating device with a second end of the reservoir block aligned with and insertable into the pass-through path, the reservoir block being movable with respect to the block container to advance the reservoir block past the heat source;
  wherein the block container includes a shell that attaches to the heating device and a manually operable block advancer that a user can operate to advance the reservoir block into the pass-through path.

16. The volatile carrier of claim 15, wherein the block advancer includes a block holder that is slidably engaged with the shell and, when a user slides the block holder relative to the shell, the user moves the reservoir block relative to the heat source.

17. The volatile carrier of claim 15, wherein the block advancer is operated by a rotatable part that is rotatably engaged with the shell and that, when that part is turned, the advancer moves the reservoir block relative to the heat source.

18. The volatile carrier of claim 17, wherein the block advancer provides a signal to a user that correlates to movement of the reservoir block as the reservoir block is advanced relative to the heat source.

19. The volatile carrier of claim 17, wherein the block advancer includes a detent mechanism that overcomeably resists turning movement of the rotatable part relative to the shell as the rotatable part is turned in successive, incremental amounts to provide a tactile signal to a user of an incremental movement of the reservoir block.

20. The volatile carrier of claim 17, wherein the block advancer includes
  a. a threaded shaft rotatably engaged but longitudinally fixed with respect to the shell, and
  b. a nut longitudinally that is fixed with respect to the reservoir block as the reservoir block is advanced and is threadably engaged with the threaded shaft to longitudinally advance the reservoir block relative to the shell when the threaded shaft is rotated with respect to the nut.

21. The volatile carrier of claim 17, wherein the block advancer includes
  a. a nut rotatably engaged but longitudinally fixed with respect to the shell, and
  b. a threaded shaft that is longitudinally fixed with respect to the reservoir block as the reservoir block is advanced and is threadably engaged with the threaded shaft to longitudinally move the reservoir block relative to the shell when the nut is rotated with respect to the threaded shaft.

22. A method of supplying a volatile ingredient to be dispensed by the heating device referred to in claim 1 comprising the steps of
  a. supplying the volatile carrier of claim 1, and
  b. moving the reservoir block past the heating device's heat source.

23. The method of claim 22, wherein the volatile carrier supplied is the carrier of claim 3 and the step of moving the reservoir block past the heating device's heat source includes the steps of selecting a region of the reservoir block carrying a desired volatile ingredient and moving that region to the heat source.

24. The method of claim 23, wherein the step of moving the reservoir block past the heating device's heat source further includes successively moving different selected regions of the reservoir block to the heat source to cause the heating device successively to emit different volatile ingredients.

25. The method of claim 22, wherein the volatile carrier supplied is the carrier of claim 4, and the step of moving the reservoir block past the heating device's heat source includes the steps of selecting a region of the reservoir block carrying a desired concentration of the volatile ingredient and moving that region to the heat source to cause the heating device to emit a selected amount of the volatile ingredient.

26. The method of claim 25, wherein the step of moving the reservoir block past the heating device's heat source further includes successively moving different selected regions of the reservoir block to the heat source to cause the heating device successively to emit differing amounts of the volatile ingredient.

* * * * *